United States Patent
Matsumoto

(10) Patent No.: US 11,967,424 B2
(45) Date of Patent: Apr. 23, 2024

(54) INFORMATION PROCESSING APPARATUS, INFORMATION PROCESSING METHOD, AND RECORDING MEDIUM

(71) Applicant: Konica Minolta, Inc., Tokyo (JP)

(72) Inventor: Hiroaki Matsumoto, Yokohama (JP)

(73) Assignee: KONICA MINOLTA, INC., Tokyo (JP)

( * ) Notice: Subject to any disclaimer, the term of this patent is extended or adjusted under 35 U.S.C. 154(b) by 605 days.

(21) Appl. No.: 17/173,560

(22) Filed: Feb. 11, 2021

(65) Prior Publication Data

US 2021/0256295 A1 Aug. 19, 2021

(30) Foreign Application Priority Data

Feb. 17, 2020 (JP) ................................ 2020-023909

(51) Int. Cl.

| | |
|---|---|
| G06V 10/80 | (2022.01) |
| G06F 18/214 | (2023.01) |
| G06F 18/2413 | (2023.01) |
| G06V 10/764 | (2022.01) |
| G06V 10/82 | (2022.01) |
| G16H 10/60 | (2018.01) |
| G16H 30/20 | (2018.01) |
| G16H 30/40 | (2018.01) |

(Continued)

(52) U.S. Cl.
CPC ........... *G16H 40/67* (2018.01); *G06F 18/214* (2023.01); *G06F 18/2413* (2023.01); *G06V 10/764* (2022.01); *G06V 10/809* (2022.01); *G06V 10/82* (2022.01); *G16H 10/60* (2018.01); *G16H 30/20* (2018.01); *G16H 30/40* (2018.01); *G16H 50/20* (2018.01)

(58) Field of Classification Search
CPC .. G06F 18/214; G06F 18/2413; G06F 18/254; G06V 10/764; G06V 10/809; G06V 10/82; G06V 2201/032; G16H 40/67; G16H 10/60; G16H 30/20; G16H 30/40; G16H 50/20; G16H 50/70
See application file for complete search history.

(56) References Cited

U.S. PATENT DOCUMENTS

2008/0292194 A1\* 11/2008 Schmidt ................. G06T 7/143
  382/131
2013/0044927 A1\* 2/2013 Poole .................... G06T 7/0014
  382/128

(Continued)

FOREIGN PATENT DOCUMENTS

| JP | 5533662 B2 | 6/2014 |
|---|---|---|
| JP | 2019-109553 A | 7/2019 |
| WO | 2019/234810 A1 | 12/2019 |

OTHER PUBLICATIONS

Office Action dated Oct. 3, 2023 for corresponding Japanese Application No. 2020-023909, with English translation.

*Primary Examiner* — Phuoc Tran
(74) *Attorney, Agent, or Firm* — Lucas & Mercanti, LLP

(57) ABSTRACT

An information processing apparatus including: a classifier that is applied for medical treatment data; and a hardware processor that sets a property of the classifier, evaluates a sufficiency level of the property by using evaluation data for the classifier, and selects and sets one classifier as the classifier to be used in a facility by referring to an evaluation result.

9 Claims, 7 Drawing Sheets

(51) Int. Cl.
 *G16H 40/67* (2018.01)
 *G16H 50/20* (2018.01)

(56) References Cited

U.S. PATENT DOCUMENTS

2018/0122508 A1* 5/2018 Wilde .................... G16H 10/40
2019/0189278 A1* 6/2019 Matsumoto ............ G06N 20/00

* cited by examiner

FIG. 8

| | ABNORMAL SHADOW DETECTION (SENSITIVITY) | | | CLASSIFY NORMAL AS NORMAL (SPECIFICITY) | PROCESSING SPEED |
|---|---|---|---|---|---|
| | NODULE | PNEUMOTHORAX | TUBERCULOSIS | | |
| PROPERTY OF CURRENT CLASSIFIER A | 80% | 60% | 90% | 70% | 0.5s/IMAGE |
| ESSENTIAL PROPERTY CONDITION | 90% OR MORE | — | — | CURRENT SPECIFICITY OR MORE | — |
| DESIRABLE PROPERTY CONDITION | — | 55% OR MORE | — | — | CURRENT SPEED OR MORE |
| PROPERTY OF NEW CLASSIFIER B | 92% | 50% | 70% | 80% | 0.6s/IMAGE |
| PROPERTY OF CLASSIFIER D IN ANOTHER FACILITY | 90% | 65% | 30% | 75% | 0.1s/IMAGE |
| PROPERTY OF NEW CLASSIFIER C | 85% | 65% | 95% | 95% | — |

FIG. 9

INFORMATION PROCESSING APPARATUS, INFORMATION PROCESSING METHOD, AND RECORDING MEDIUM

CROSS-REFERENCE TO RELATED APPLICATIONS

The entire disclosure of Japanese Patent Application No. 2020-023909 filed on Feb. 17, 2020 is incorporated herein by reference in its entirety.

BACKGROUND

Technological Field

The present invention relates to an information processing apparatus, an information processing method, and a recording medium.

Description of the Related Art

In a medical field, a doctor checks medical treatment data (medical information) obtained by various examinations and reads whether or not various abnormalities exist from the examination results, to conduct medical treatment.

For example, when the medical treatment data is a medical image, the medical image generated by a modality such as a CR (Computed Radiography) apparatus, an FPD (Flat Panel Detector) apparatus, a CT (Computed Tomography) apparatus, and an MRI (Magnetic Resonance Imaging) apparatus is displayed on a display (monitor), and the doctor observes the state of the lesion part and its change over time and the like, which is diagnosis by image interpretation.

However, the doctor needs to spend his/her huge amount of labor to check all pieces of medical treatment data. Thus, in order to support such diagnosis by doctor, various diagnosis support systems have been invented.

For example, JP 5533662 B2 suggests, as a method for supporting diagnosis by the doctor, an information processing apparatus that forms a classifier by learning which uses learning data and automatically checks the medical treatment data with the classifier.

JP 5533662 B2 discloses, when there are a plurality of classifiers, calculating the discrimination accuracy for each of the classifiers by using the evaluation data, and applying the optimum classifier which is most excellent in the discrimination accuracy.

In such a way, by applying the classifier which is excellent in the discrimination accuracy and forming the information processing apparatus for supporting the diagnosis by doctor, it can be expected to make the check result of the medical treatment data which is automatically performed in the apparatus be reliable.

SUMMARY

However, the performance which is required of the information processing apparatus for supporting diagnosis by a doctor (for example, type of lesion to be detected, type and degree of detection performance required for the target to be detected, and the like) varies for each medical institution (facility). Thus, the "optimum classifier" applied to the information processing apparatus is not unambiguous, and a different property is required for each medical institution using the classifier.

That is, the property of classifier includes the detection target to be detected and the detection performance for each detection target. For example, when the medical institution is specifically designed for diagnosis of cancer, the required classifier is a classifier which has a high detection performance when the detection target is a cancer.

Furthermore, the detection performance includes the sensitivity that is a probability of classifying the data including abnormality as abnormal and the specificity that is a probability of classifying normal data as normal. How much accuracy is required for each of the sensitivity and the specificity is different for each medical institution.

For example, when the required accuracy is such a degree that the doctor or the like basically checks all pieces of data (for example, images) and merely refers to the automatic discrimination results using the classifier in order to prevent the oversight, wrongly determining the normal data as abnormal does not matter too much since the wrong determination can be noticed when the doctor or the like actually sees and confirms the data. On the other hand, for example, when an image including an abnormal shadow is wrongly determined as normal, oversight by the doctor or the like may overlap the oversight in the automatic discrimination result, and the lesion or the like may be oversighted. Thus, a high sensitivity is required, while the specificity is not required so much.

As in the medical check, when a large quantity of data is obtained, most of the data is normal data and abnormal data such as the image including an abnormal shadow is mixed rarely, data which was determined as normal by automatic discrimination using the classifier may be excluded from the target of check (image interpretation) by the doctor or the like to reduce the data actually confirmed by the doctor or the like. In such a case, when the abnormal data such as an image including an abnormal shadow is wrongly determined as normal by the automatic discrimination using the classifier, the abnormal data is excluded from the check (image interpretation) target, missing the opportunity to be checked by the doctor or the like. On the other hand, when the normal data cannot be correctly determined as normal, it is not possible to decrease the check (image interpretation) target by the doctor, and not possible to appropriately achieve the role of reducing the burden on the doctor or the like. Thus, a high accuracy for sensitivity is required and a high accuracy for specificity is also required.

In such a way, the classifier applied to the information processing apparatus can have a different property required according to the situation in which the classifier is used by the user, or the like, that is, how the individual medical institution intends to use the classifier.

Thus, when the classifier is selected and set without considering the required property, there is a possibility that a classifier which is not appropriate for the medical institution is set even when the classifier is generally considered as having a high accuracy.

The present invention has been made in consideration of the above matters, and an object of the present invention is to provide an information processing apparatus, an information processing method and a recording medium that can set a classifier appropriate for a facility which uses the classifier according to the property required in the facility.

To achieve at least one of the abovementioned objects, according to an aspect of the present invention, an information processing apparatus reflecting one aspect of the present invention is an information processing apparatus including: a classifier that is applied for medical treatment data; and a hardware processor that sets a property of the classifier, evaluates a sufficiency level of the property by using evaluation data for the classifier, and selects and sets one classifier as the classifier to be used in a facility by referring to an evaluation result.

To achieve at least one of the abovementioned objects, according to another aspect of the present invention, an information processing method reflecting one aspect of the present invention is an information processing method including: property setting that is setting a property of a classifier applied for medical treatment data; evaluating that is evaluating a sufficiency level of the property by using evaluation data for the classifier; and classifier setting that is selecting and setting one classifier as the classifier to be used in a facility by referring to an evaluation result of the evaluating.

To achieve at least one of the abovementioned objects, according to another aspect of the present invention, a recording medium reflecting one aspect of the present invention is a non-transitory recording medium storing a computer readable program causing a computer of an information processing apparatus to perform: property setting that is setting a property of a classifier applied for medical treatment data; evaluating that is evaluating a sufficiency level of the property by using evaluation data for the classifier; and classifier setting that is selecting and setting one classifier as the classifier to be used in a facility by referring to an evaluation result of the evaluating.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein:

FIG. 8 is a view showing an example of a list screen of evaluation results in the present embodiment; and FIG. 9 is a view showing an example of switching/setting screen of the classifier in the present embodiment.

DETAILED DESCRIPTION OF EMBODIMENTS

Hereinafter, one or more embodiments of the present invention will be described with reference to the drawings. However, the scope of the invention is not limited to the disclosed embodiments or the illustrated examples.

Hereinafter, with reference to FIGS. 1 to 9, an embodiment of an information processing apparatus, an information processing method and a recording medium according to the present invention will be described.

Through various technically preferable limitations to implement the present invention are provided to the embodiment described below, the technical scope of the present invention is not limited to the following embodiment or the illustrated examples.

The information processing apparatus in the present embodiment is provided in a medical image system, and processes medical treatment data (medical treatment information including medical image data or the like, medical information) obtained by various types of modalities.

[Medical Image System]

Figure 1:
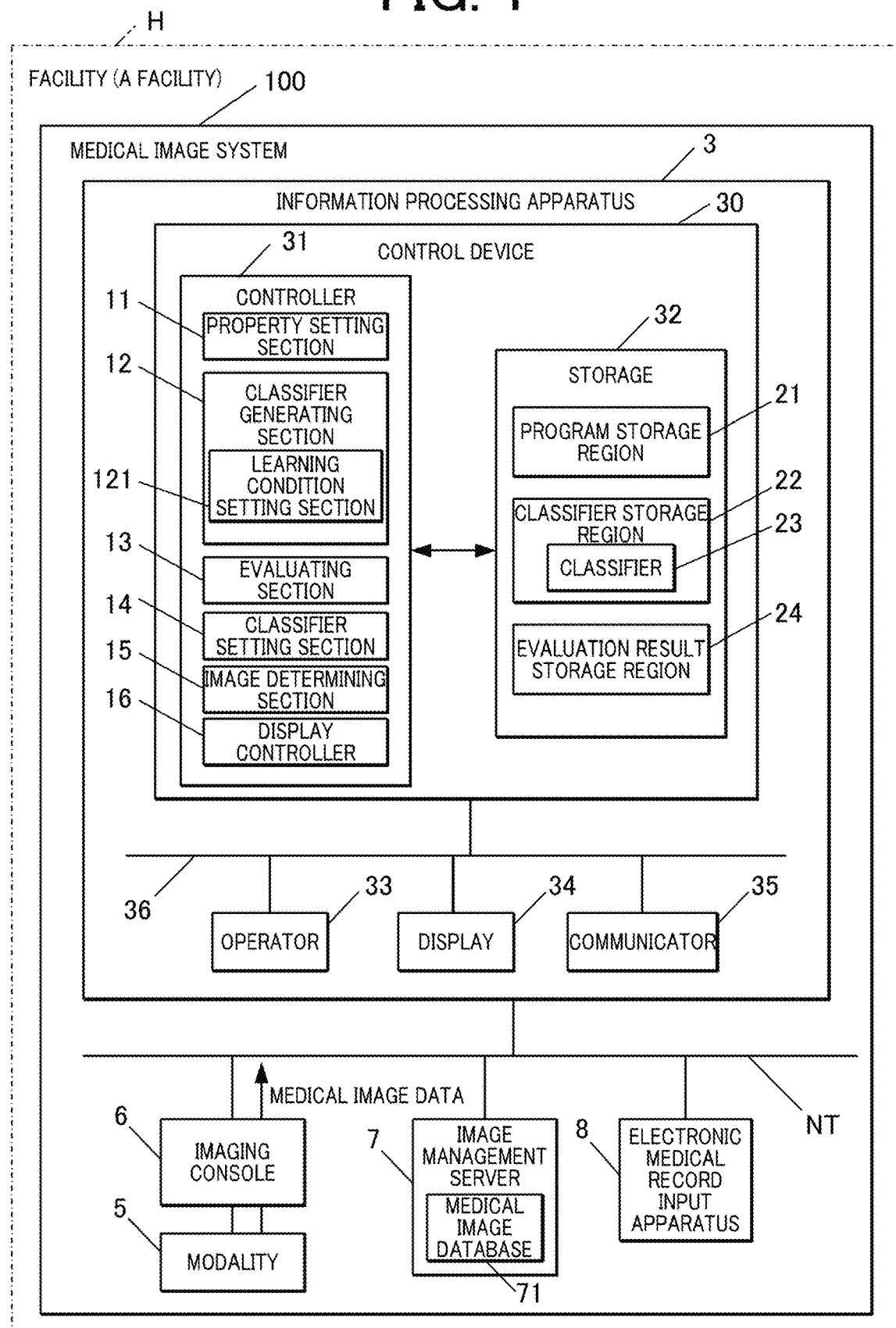
FIG. 1 is a main part configuration view showing a system configuration of a medical image system including an information processing apparatus in a present embodiment.

FIG. 1 is a main part configuration view showing a system configuration of the medical image system including the information processing apparatus in the present embodiment.

As shown in FIG. 1, a medical image system 100 is provided in a facility H ("A facility" in FIG. 1) which is a medical institution. The medical image system 100 performs imaging for examination of a patient and generates and manages medical image data and the like as medical treatment data.

In the present embodiment, as the facility H which is a medical institution, a general clinic, a clinic practiced personally by a practicing doctor, a relatively small scale medical facility such as a clinic, a doctor's office or the like is assumed.

The facility H which is the medical institution is not limited to the facilities described above as long as the facility H handles a medical image or the like as medical information.

The medical image system 100 includes: various modalities or a modality (image generating apparatus) 5 that generates a medical image; an imaging console 6 that controls an imaging operation by the modality 5; an image management server 7 that includes a medical image database 71 and stores and manages medical image data and the like obtained by the modality 5; an electronic medical record input apparatus 8; and an information processing apparatus 3 that determines whether or not the medical image includes abnormal data (for example, abnormal shadow). The imaging console 6 connected to the modality 5, the image management server 7, the electronic medical record input apparatus 8 and the information processing apparatus 3 are connected to a network NT1 via a switching hub or the like not shown in the drawings, and data can be transmitted and received via the network NT1.

The apparatuses connected via the network NT1 and forming the medical image system 100 are based on DICOM (Digital Image and Communications in Medicine) standard that is a communication standard treating medical data generally, for example. The communication between the apparatuses is performed on the basis of DICOM. The number of apparatuses is not particularly limited.

The elements forming the medical image system 100 are not limited to the elements described above, and the elements may include other storages, servers, and the like.

It is not essential that the medical image system 100 includes the image management server 7 and the electronic record input apparatus 8. For example, the image management server 7 and/or the like may be provided outside the medical image system 100 to be able to transmit and receive data via an external network not shown in the drawings.

The modality 5 provided in the medical image system 100 takes an image of an examination target site of a patient, and performs digital conversion of the taken image to generate medical image data or the like as medical information.

As the modality 5, for example, a CR (Computed Radiography, X-ray simple imaging) apparatus, an FPD (Flat Panel Detector) apparatus, a mammography apparatus, a CT (Computed Tomography) apparatus, an ultrasound diagnostic apparatus, an endoscope apparatus, and the like are assumed, but the modality 5 is not limited to these apparatuses.

Though FIG. 1 illustrates only one set of modality 5 and imaging console 6, a plurality of modalities 5 and the like may be provided in the medical image system 100. In such a configuration, a same type of modalities 5 may be provided, or different types of modalities 5 may be provided.

When the apparatuses forming the medical image system 100 are based on the DICOM standard, the image data of a medical image (medical image data) is stored in a DICOM file format based on the DICOM standard. The DICOM file is formed of an image section and a header section. Actual data of the medical image is written to the image section, and accompanying information related to the medical image is written to the header section. In the present embodiment, the medical image data and its accompanying information (accompanying information, additional information) are collectively referred to as "medical treatment data".

The accompanying information is formed by including patient information, examination information and detailed image information, for example.

The patient information includes various type of information regarding a patient of the medical image such as patient identification information for identifying the patient (for example, patient ID), patient name, sex, birth date and the like.

The examination information includes various type of information regarding an examination such as examination identification information for identifying the examination (for example, examination ID), examination date, type of modality, examination site, and the doctor in charge.

The detailed image information includes various types of information regarding the medical image such as an image ID, an image generation time, and a file path name indicating the location storing the medical image.

The medical image data obtained by the modality 5 is transmitted to the image management server 7 connected to the network NT1 via the imaging console 6, and stored in the medical image database 71 or the like together with its accompanying information.

When the medical image is not in a format based on the DICOM, it is preferable that the medical image is stored in the medical image database or the like after converting the format into a format based on the DICOM and/or adding a UID (unique ID) for individually specifying the medical image to the medical image.

The image management server 7 is a computer apparatus that accumulates and stores and manages image data (medical image data) of the medical image generated by the modality 5 and the accompanying information regarding the medical image (medical treatment data which is medical information).

To be specific, the image management server 7 has the medical image database 71 formed of a hard disk or the like.

As mentioned above, the medical image data stored in the medical image database 71 is saved in a DICOM file format based on the DICOM standard.

The DICOM file is formed of an image section and a header section. The medical image database 71 has a medical image management table storing the accompanying information of the medical image and stores the medical image to be searchable.

When the image management server 7 receives the medical image from the modality 5, the image management server 7 stores the received medical image in the medical image database 71, and registers its accompanying information in the medical image management table.

The image management server 7 has a storage (electronic medical record information database) (not shown in the drawings) which stores the electronic medical record which was input from the electronic medical record input apparatus 8.

In the electronic medical record information database of the image management server 7, there are stored respective items of patient information such as the patient ID, name, sex, age, weight, height, body temperature, medical questionnaire results and entry date (writing date).

The electronic medical record input apparatus 8 is an apparatus for inputting electronic medical record information such as the patient information and the medical questionnaire results.

The information (electronic medical record information) input from the electronic medical record input apparatus 8 is stored in the medical image database 71 so as to be associated with the medical image data.

The electronic medical record information is, for example, respective items of patient information such as the patient ID, name, sex, age, weight, height, body temperature, medical questionnaire results, and the entry date, but not limited to them.

[Information Processing Apparatus]

The information processing apparatus 3 detects whether or not the medical treatment data including the medical image data which is the medical information includes any abnormal shadow which is abnormal data, and supports the diagnosis by the doctor or the like.

In the present embodiment, the information processing apparatus 3 includes a control device 30, an operator 33, a display 34, a communicator 35 and the like, and these components are connected via a bus 36.

The operator 33 is configured by including a keyboard that includes a cursor key, numerical input keys and various types of function keys and a pointing device such as a mouse, for example. The operator 33 outputs an instruction signal input by a key operation performed to the keyboard and a mouse operation to the control device 30.

The display 34 is configured by including a monitor such as an LCD (Liquid Crystal Display) and a CRT (Cathode Ray Tube), and displays various types of screens, medical images and the like in accordance with the instruction of the display signal input from the control device 30.

The display 34 may be integrally configured with a touch panel. In such a configuration, a signal indicating the touched position on the touch panel is transmitted to the controller 31, and the touch panel functions as an operator 33.

The communicator 35 includes a LAN adapter, a router, a TA (Terminal Adapter) and the like, and performs data transmission and reception with each of the apparatuses connected to the network NT1.

The control device 30 in the information processing apparatus 3 includes a controller 31 that is configured by a CPU not shown in the drawings and the like, and a storage 32 that is configured by a ROM, a RAM and the like not shown in the drawings.

The control device 30 is a computer that has the controller 31 read out various types of programs stored in the ROM of the storage 32 and loads them to a working area of the RAM, and achieves the various types of functions in cooperation with the programs.

In the present embodiment, in a function view, the controller 31 includes a property setting section 11, a classifier generating section 12, an evaluating section 13, a classifier setting section 14, an image determining section 15, a display controller 16 and the like.

The property setting section 11 is a property setting section that sets the property of the classifier 23.

The "property" here indicates the "detection target" to be detected by applying the classifier 23 and the "detection performance" for the detection target. The "property" may include at least one of them. In the present embodiment, the "property" includes both of the "detection target" and the "detection performance" for the detection target.

The detection target is, for example, the type of lesion when the presence/absence of the abnormal shadow which is the lesion part is detected from the medical image as in the present embodiment. The type of lesion which can be detected by the classifier 23 is not particularly limited. For example, the classifier 23 may be able to classify ten types or more of lesions, and particularly accurately detect limited two or three types of lesions (for example, nodule, pneumothorax, and tuberculosis) among the lesions.

The detection performance is "sensitivity" that is a probability of classifying data including abnormality as abnormal and "specificity" which is a probability of classifying normal data as normal. The detection performance may include at least one of them. In the present embodiment, the detection performance includes both of the "sensitivity" and the "specificity".

The details of a method of setting the property of classifier 23 by the property setting section 11 will be described later.

As for the classifier 23 stored in the storage 32 (aftermentioned classifier storage region 22), the classifier generating section 12 generates a new classifier 23 by performing learning (machine learning).

The classifier 23 is applied to medical treatment data (data for medical treatment) which is medical information. In the present embodiment, by applying the classifier 23 to data of the medical image used in image diagnosis or the like, the discrimination result regarding whether the data is "abnormal image" that includes an abnormal shadow indicating the lesion part or "normal image" that does not include the abnormal shadow is output.

In the present embodiment, the classifier 23 assists diagnosis by the doctor by automatically discriminating whether the data of the medical image is "abnormal image" including an abnormal shadow or "normal image" not including the abnormal shadow.

In an initial state of the information processing apparatus 3, the classifier 23 is a general-purpose classifier 23 which is set at the factory, for example.

In the initial state of the information processing apparatus 3, instead of the general-purpose classifier 23, there may be installed a classifier 23 which already has an experience of being used in the information processing apparatus 3 or the like of anther facility H (for example, B facility different from the present A facility). This configuration is preferable since the discrimination accuracy according to the nature of facility H can be expected to some degree from the initial stage, by introducing the classifier 23 which has been used at the facility H (for example, facility H which treats many patients close to an age group of patients expected to use the A facility H) having the nature close to the nature of facility H (for example, A facility) which newly introduces the information processing apparatus 3.

The classifier 23 is formed by repeating learning (machine learning) using learning data.

As such a machine learning method, for example, there is used a segment recognition method using deep learning such as CNN (Convolutional Neural Network).

The learning method is not particularly limited as long as the method can generate a classifier 23 that can appropriately classify the medical treatment data which is the medical information. That is, the method of learning (machine learning) of the classifier 23 is not limited to deep learning, and may be, for example, AdaBoost (or its multi-value type AdaBoostMlt), artificial neural network, support vector machine, Bayesian learning (for example, variational Bayesian method) and an EM (Expectation-Maximization) algorism as the method using clustering by mixture distribution, and may be combinations combining these methods with deep learning.

As learning data of initial setting, a large amount of general-purpose data which is balanced in data tendency is used.

In the present embodiment, the classifier generating section 12 includes a learning condition setting section 121. The learning condition setting section 121 is a learning condition setting section that sets a learning condition of the classifier 23.

In the present embodiment, the setting of learning condition by the learning condition setting section 121 is performed on the basis of the property of classifier 23 set by the property setting section 11.

The learning data used in learning of the classifier 23 is sorted on the basis of the property of the classifier 23, and the learning condition setting section 121 extracts learning data according to the property of classifier 23 set by the property setting section 11.

The details of setting of the learning condition by the learning condition setting section 121 will be described later.

The learning data and after-mentioned evaluation data for evaluating the learning results are associated with information on presence/absence of abnormality such as abnormal shadow.

The learning of classifier 23 using the learning data and calculation of discrimination accuracy of the classifier 23 using the evaluation data are performed on the basis of information on presence/absence of various abnormalities associated with the learning data and the evaluation data.

That is, the information on presence/absence of abnormality associated with each piece of data is correct answer information on whether or not each piece of learning data and evaluation data includes abnormal data, and what kind of abnormal data is included if the data includes abnormal data. At the time of learning of classifier 23 and calculation of discrimination accuracy of the classifier 23, and whether or not the classifier 23 could correctly discriminate such information is evaluated.

The information regarding presence/absence or the like of abnormal shadow is associated with corresponding learning data and evaluation data on the basis of the results of image interpretation by the doctor or the results of definite diagnosis when the definite diagnosis is obtained by other examination or the like, for example.

The evaluating section 13 is an evaluating section that evaluates the sufficiency level of property by using the evaluation data for the classifier 23. In the present embodiment, the evaluating section 13 evaluates the sufficiency level of property for each of a plurality of classifiers 23. The evaluation result of discrimination accuracy of each classifier 23 by the evaluating section 13 is stored in the evaluation result storage region 24 of the storage 32.

In the present embodiment, the evaluating section 13 performs evaluation for each of the classifiers 23 by using the evaluation data, from two viewpoints that are a rate of being able to discriminate an abnormal shadow and a rate of wrongly recognizing the normal image as the image including an abnormal shadow, and calculates each discrimination accuracy.

The classifier setting section 14 is a classifier setting section that sets one classifier 23 as the classifier 23 to be used for discrimination of presence/absence of abnormal data (abnormal shadow) on the basis of the calculation result by the evaluating section 13. In the present embodiment, one classifier 23 is set as the classifier 23 to be used in the present facility H (for example, A facility) from among a plurality of classifiers 23 (for example, classifier B, classifier C, classifier D, etc. in FIG. 5).

To be specific, for example, on the basis of the calculation result by the evaluating section 13, the user operates the operator 33 or the like to select and input the classifier 23 to be used in the facility H. When this selection/input result is output to the control device 30, the classifier setting section 14 receives the selection result and sets the classifier selected by the user as the classifier to be used for discrimination of presence/absence of abnormal data (abnormal shadow) or the like in the facility H. That is, when a classifier (for example, one of the classifiers B, C and D) other than the classifier 23 (for example, classifier A) which is currently used in the facility H is selected, the classifier 23 is switched to the selected classifier.

The image determining section 15 is an image determining section that applies the classifier 23 (learned classifier 23) which was set by the classifier setting section 14, and determines whether actual medical treatment data (data of an unknown medical image) is the "abnormal image" including an abnormal shadow or the "normal image" not including the abnormal shadow.

That is, the image determining section 15 inputs the medical image data or the like which was obtained by the modality 5 and stored in the image management server 7 to the classifier 23 (learned classifier 23), and outputs the determination result regarding the data.

The display controller 16 is a display controller that controls the display 34 to display various images such as the medical image to be interpreted and various types of information.

In the present embodiment, the display controller 16 controls the display 34 to display information on the discrimination accuracy calculated for the classifier 23 by the evaluating section 13.

To be specific, the display 34 displays the property of classifier 23 and the evaluation result by the evaluating section 13 for each of the classifiers 23.

It is preferable that the display controller 16 controls displaying of the display 34 to use different displaying methods when the evaluation result satisfies the property of the classifier set by the property setting section 11 and when the evaluation result does not satisfy the property.

The specific displaying example (see FIG. 8) will be described later.

The storage 32 stores data or the like necessary for the information processing apparatus 3 to perform various types of processing. In the present embodiment, the storage 32 includes various storage regions such as a program storage region 21, a classifier storage region 22 storing the classifier 23, and an evaluation result storage region 24 storing the evaluation result by the evaluating section 13.

The storage 32 may include storage region(s) other than the regions illustrated in FIG. 1, and all or a part of the storage regions illustrated in FIG. 1 may be provided outside the storage 32.

The storage storing the data and programs necessary for the information processing apparatus 3 to perform various types of processing, the classifier 23 and the like is not limited to the storage provided in the information processing apparatus 3 as shown in FIG. 1. For example, an external server such as a cloud server that provides a "cloud computing service" to the user may be used as the storage.

The program storage region 21 is a region for storing various programs necessary for the controller 31 to control the components of the information processing apparatus 3. In the present embodiment, for example, the program storage region 21 stores a program for setting the property of classifier, a program for evaluating the sufficiency level of the property by using the evaluation data for the classifier 23, a program for referring to the evaluation result by the evaluating section 13 and selecting and setting one classifier 23 from among a plurality of classifiers 23 as the classifier 23 to be used in the facility, and the like.

The classifier storage region 22 stores a plurality of classifiers 23 such as a general-purpose classifier 23 that is set in the initial state of the information processing apparatus 3 and a classifier 23 which was newly generated by the learning (machine learning) after the initial state.

The evaluation result storage region 24 is a region storing the evaluation result of the discrimination accuracy of each classifier by the evaluating section 13. The evaluation result is stored to be associated with each classifier 23.

[Action of Information Processing Apparatus (Information Processing Method)]

Next, with reference to FIG. 2, the processing executed by the information processing apparatus 3 in the present embodiment will be described.

Figure 2:
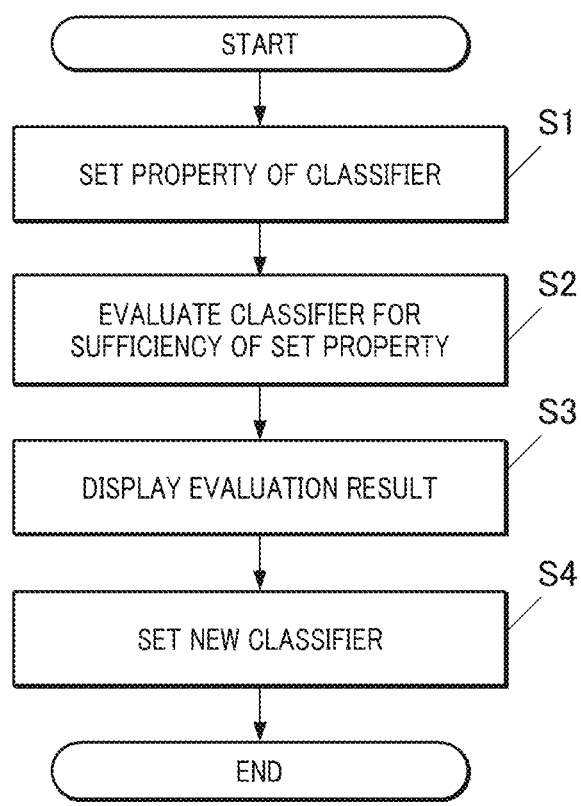
FIG. 2 is a flowchart showing a procedure of an information processing method in the present embodiment.

As shown in FIG. 2, in the present embodiment, the property setting section 11 sets the property of the classifier 23 to be applied in the information processing apparatus 3 according to the nature (for example, what kind of lesion to be detected, what kind of detection performance and what degree of the detection performance are necessary for the target to be detected, and the like) required of the information processing apparatus 3 in the present facility H (for example, A facility) (step S1).

The property of the classifier 23 includes the "detection target" and "detection performance" as mentioned above, and the "detection performance" includes the "sensitivity" that is a probability of classifying data including abnormality as abnormal and the "specificity" that is a probability of classifying normal data as normal.

The way to set the property is not particularly limited. However, for example, an average value is set as a default value for the property required of the classifier 23 in the initial state, and when the user specifies the item especially requiring accurate detection, the property according to the specified item is set by the property setting section 11.

To be specific, for example, when the display 34 is caused to display a setting screen or the like not shown in the drawings and the user specifies the "detection target" for which the user desires discrimination with an especially high accuracy by performing a touch operation of touching the screen or performing an input operation from the operator 33, the instruction signal is output to the controller 31 and setting in accordance with the instruction signal is performed.

Similarly, how much degrees of "sensitivity" and "specificity" are required as the "detection performance" can also be specified by the user with the touch panel formed on the display 34, the operator 33 or the like so that when the instruction signal corresponding to user's operation is output to the controller 31, the setting in accordance with the instruction signal is performed.

For example, when there are a dozen (ten and several) types of lesions (abnormal shadows) which can be discriminated by the classifier 23 and it is sufficient that especially three types of nodule, pneumothorax, and tuberculosis among the lesions can be discriminated in the present facility H (for example, A facility), the display 34 is caused to display a list of lesion types, and the user selects nodule, pneumothorax, and tuberculosis from among the lesion types. Then, the nodule, pneumothorax, and tuberculosis are set by the property setting section 11 as the properties (detection target) required of the classifier 23. When the detection target is limited to the three types of lesions (abnormal shadows) which highly need to be discriminated in the present facility H (A facility) in such a way, the detection accuracy is not required for the other lesions (abnormal shadows) which do not highly need to be discriminated in the present facility H (A facility), and instead, it can be expected to achieve higher detection accuracy for the detection targets which highly need to be discriminated.

As for each detection target (in the above example, nodule, pneumothorax, and tuberculosis), the user can input, from the touch panel on the display screen or the operator 33, the degree of sensitivity (probability of classifying data including abnormality as abnormal) of an abnormal shadow and the degree of specificity (probability of classifying normal data as normal). When the instruction signal according to user's operation is output to the controller 31, the setting according to the instruction signal is performed.

Thus, for example, the property setting section 11 sets the property (detection target and detection performance) of the classifier 23 to be a value meeting user's demand, merely by the user inputting items such as the sensitivity of 90% or more when the detection target is nodule, the sensitivity of 60% or more when the detection target is pneumothorax, and the sensitivity of 80% or more and the specificity of 70% or more when the detection target is tuberculosis.

The items which have no special instruction by the user are set to maintain the default value or the current value. It is preferable that each of the items which were not especially specified by the user has its preset value or current value as the minimum value and the property of the classifier 23 for the item is set not to be lower than the minimum value. Thus, it is possible to reduce the trouble for the user to individually set each of the sensitivity of classifying the abnormal shadow and the specificity of classifying the normal image as normal, and set the property meeting user's demand while reducing the burden on the user.

The items which can be set as the property of classifier 23 may include a processing speed.

The processing speed is set such that the processing speed per image is less than 0.5 second, for example. Thus, it is possible to obtain the classifier 23 of the processing speed desired by the user. The minimum value (allowable slowest value) of the processing speed may be set so as to avoid setting of classifier having an extremely slow processing speed.

The processing speed may be set for each detection target. Among the detection targets, there are lesions requiring an urgent response such as diagnosis by the doctor, various types of treatments and the like immediately after finding the abnormality. For such a detection target (lesion (abnormal shadow)) requiring an urgent response, it is possible to have the classifier 23 of the property meeting user's demand by enabling individual setting such as setting the processing speed to be especially high.

The way to set the property of the classifier 23, the settable contents, and the like are not limited to the above examples.

For example, even when the user does not input, the cases which have been treated at the present facility (for example, A facility) before may be analyzed so that the values of detection performance (sensitivity and specificity) are automatically set high for the detection targets which are top in the treating record.

The detection target is not limited to the individual lesion such as the nodule, pneumothorax, and tuberculosis. For example, the detection target may be selected and set as an item which is grouped to some degree, such as the lesion regarding lungs, lesion regarding internal organs, and the lesion regarding circulatory organ system. Thus, it is possible to more reduce the burden on the user at the time of property setting.

Furthermore, the specification of the values of detection performance (sensitivity and specificity) by the user is not limited to the specification way of inputting the percentage. For example, rough specification such as high/medium/low may be allowed. In this configuration, the property setting section 11 correlates and recognizes the input by the user with the specific numerical value and sets the specific numerical value of the property, such as 90% or more for "high", 80% or more for "medium", and less than 80% for "low".

For example, for the detection performance (specificity), the average of the numbers of wrong detection per image (FPPI) may be set to be equal to or less than 0.1. In this configuration, the frequency of wrongly detecting the normal data ("normal image") as data including abnormality ("abnormal image") can be set to a value desired by the user.

There may be set that even the detection target having the lowest sensitivity among the plurality of selected detection targets (lesions (abnormal shadows)) has its minimum value being a predetermined value (for example, 80%) or more. In this configuration, even when the user does not input all the detection performances (sensitivities) of the plurality of detection targets (lesions (abnormal shadows)), it is possible to set the property of classifier 23 to a value desired by the user.

The property setting section 11 in the present embodiment performs setting by dividing the conditions to an essential property condition (hereinafter, referred to as "essential property condition") which is definitely required and a property condition (hereinafter, referred to as "desirable property condition") which is not definitely required. This helps consideration when the user compares after-mentioned evaluation results of evaluation performed to each of the classifiers 23 by the evaluating section 13, and helps determination when the user selects the classifier 23 which has the property meeting the demand.

After the property of the classifier 23 is set by the property setting section 11, candidates of classifier 23 to be used in the present facility H are prepared on the basis of the set property.

To be specific, in order to have the classifier 23 which has the set property, learning of the classifier 23 is performed in the classifier generating section 12, and the learned classifier 23 is generated. The generated classifier 23 is stored in the classifier storage region 22 or the like of the storage 32.

The learning is performed by machine learning (deep learning) applying a neural network (hereinafter, simply referred to as "network") as mentioned above, for example.

Figure 3:
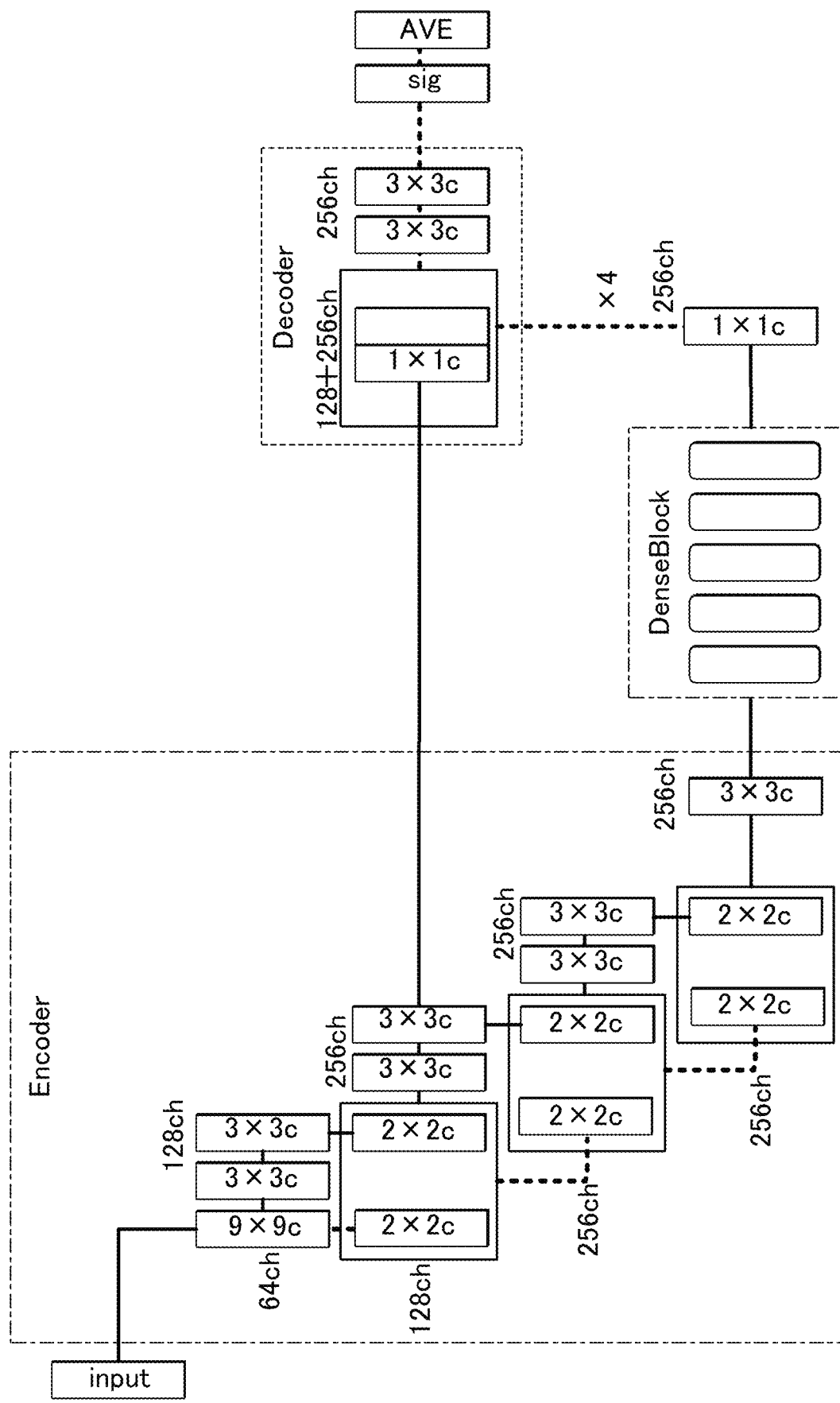
FIG. 3 is a view showing an example of a network applied to a classifier in the present embodiment.

FIG. 3 shows an example of the network structure.

FIG. 3 shows a configuration example of a network specializing in region recognition of an image, in which a plurality of convolutional layers is provided, and in response to input of an input image, the kernel (filter) is applied to the convolutional layers to perform the convolutional operation and thereby a feature amount is extracted from the image, and a certainty image which has each pixel representing the certainty corresponding to the abnormal shadow is output as an output image. In the example shown in the present embodiment, when the maximum value of the output certainty image (output image) exceeds a threshold value, the input image is determined as an "abnormal image" which includes an abnormal shadow.

In FIG. 3, the "1x1c" indicates the convolutional layer of 1x1x (input channel number), and "3x3c" indicates the convolutional layer of 3x3x (input channel number). The "2x2c" means 2x2x (input channel number), and indicates the convolutional layer to be skipped every other pixel (as a result, thinned out to a half image size). Similarly, the "9x9c" means 9x9x (input channel number), and indicates the convolutional layer to be skipped every other pixel (as a result, thinned out to a half image size).

The "DenseBlock (Densenet)" is formed of a plurality of processing blocks, and functions as the entire combining layer having the feature map connecting all the outputs of "Encoder" before this as input to the layer after this.

As for the value input to "Decoder" from "DenseBlock", the output value indicating the certainty of whether it is the abnormal shadow or not is determined through the activating function. FIG. 3 illustrates "sig (sigmoid function)" as the activating function, but the activating function is not limited to this.

In the present embodiment, as shown in FIG. 3, the averaging filter (AVE layer, referred to as "AVE" in FIG. 3) is applied to the output value determined through the activating function. In the network of the present embodiment, the certainty (certainty image) corresponding to the abnormal shadow is output for each pixel as mentioned above, but a fine resolution is not necessary in the detection of abnormal shadow (lesion part), and thus, averaging has no problem. Furthermore, by applying the averaging filter to the certainty image (output image) and thereafter determining whether or not the image is an "abnormal image" including an abnormal shadow (lesion part) for the maximum value of the certainty image, there is an effect that it is possible to reduce the wrong detection that has a high certainty corresponding to an abnormal shadow for the normal region (normal image). Thus, in the present embodiment, the averaging filter is applied to perform the final output.

The network configuration shown in FIG. 3 is an example, and the network which can be applied to the present embodiment is not limited to the illustrated example.

For example, various convolutional neural networks such as U-Net may be applied.

When it is sufficient that the determination of whether or not the input image is an "abnormal image" including the abnormal shadow can be performed, for example, a network of a configuration not including "Decoder" as in VGG can be adopted.

In the present embodiment, as mentioned later, the loss (Loss) is calculated to evaluate the classifier 23. When calculating the loss, there is applied a network of a configuration which can output the certainty image as the final output.

It is preferable that the learning (machine learning (deep learning)) is performed by using the data collected in the present facility H (for example, A facility) which is the facility to use the classifier 23. That is, when a large amount of learning data used for learning of classifier 23 is obtained in the present facility H, by performing learning with as much data obtained in the present facility H as possible, it can be expected to have the classifier 23 more corresponding to the property according to the present facility H.

The learning data is not limited to the data obtained in the present facility H. For example, learning may be performed by using the data collected in another facility H different from the present facility H to use the classifier 23. When there is not much data which can be obtained in the present facility H and it is not possible to sufficiently secure the learning data used for learning of the classifier 23, learning may be performed with the data obtained in another facility H. In this configuration, it is preferable to use data of a facility which has conditions and environment having a tendency in age group of patient and in type of lesion of patient, the tendency being as close to the tendency of the present facility H as possible.

The learning data is not limited to the data based on actual data. When the sufficient number of data to perform learning cannot be secured by the actual data only, pseudo data may be generated by deep learning with the data collected in the present facility H (if not sufficient, data collected in another facility H) as original data. The method to generate the pseudo data is not particularly limited. For example, data having a common feature as the original data is generated as the pseudo data on the basis of the original data by the image data generating section such as GAN (DCGAN; Deep Convolutional Generative Adversarial Networks).

The evaluation data used for evaluating the sufficiency level of property of classifier 23 is similar to the above learning data. That is, also for the evaluation data, it is preferable to use the data collected in the present facility H (for example, A facility), but the data collected in another facility H, the pseudo data or the like generated by the image data generating section (not shown in the drawings) may be used.

In the present embodiment, the learning condition when performing learning of a plurality of classifiers 23 is automatically set by the learning condition setting section 121 on the basis of the property of classifier 23 set by the property setting section 11 as mentioned above.

In order to perform learning so that the classifier 23 has a desired property, it is necessary to appropriately set the learning condition. However, it is difficult and troublesome for the user to determine and set what to adjust and how to adjust to obtain the classifier 23 that satisfies the desired property.

In this point, in the present embodiment, when the property of classifier 23 is set by the user specifying the desired property of classifier 23, the learning condition is automatically set so as to obtain the classifier 23 having the set property.

A large amount of learning data is used for learning of the classifier 23. The result of the learning is influenced by the configuration of the learning data.

For example, the input image which is input includes an "abnormal image" including an abnormal shadow and a "normal image" not including abnormal shadow. When the input image includes many "normal images", determination as "normal" for most cases leads to the correct answer. Thus, when the learning of classifier 23 is performed by using the learning data including many "normal images", the learning result is that the "specificity" which is a probability of classifying the normal data as normal is high, while the "sensitivity" which is a probability of classifying the data including abnormality as abnormal is low. Thus, when the user desires the classifier 23 having a high "sensitivity" as the property, it is necessary to perform learning of classifier 23 by using learning data including many "abnormal images".

Thus, it is necessary to optimize the configuration of learning data by adjusting the proportion of "normal image" and "abnormal image" regardless of the original ratio of "normal image" and "abnormal image" forming a plurality of pieces of learning data (learning data group). In the present embodiment, as the setting of learning condition by the learning condition setting section 121, the learning data used in learning is adjusted according to a desired property.

Figure 4:
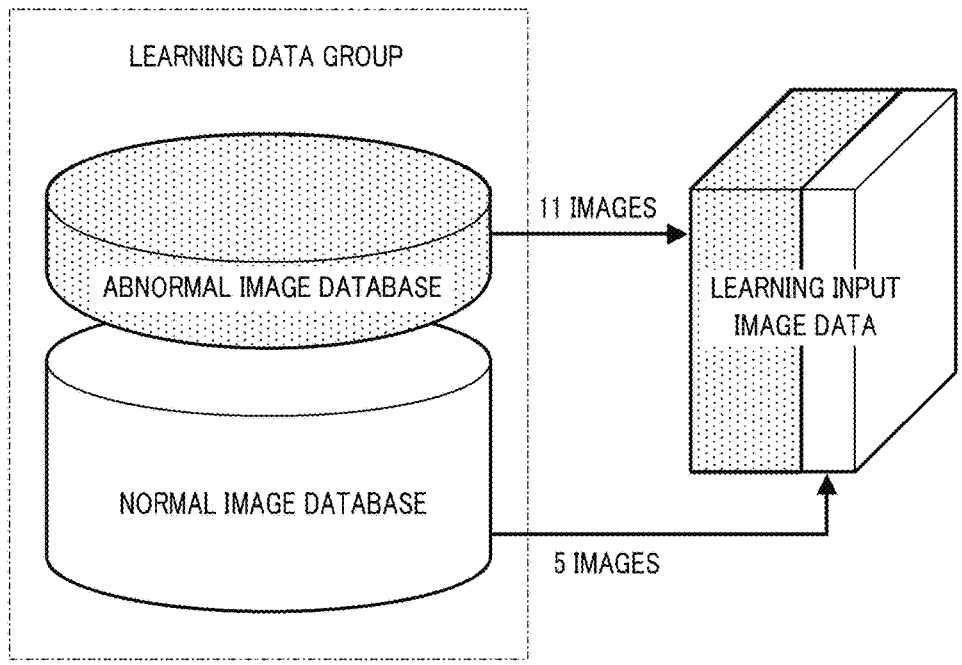
FIG. 4 is an explanation view schematically showing a configuration example of input data for learning of the classifier.

FIG. 4 shows a data configuration example of learning data stored in the image management server 7 or the like. As shown in FIG. 4, the learning data (learning data group) used in learning of the classifier 23 is sorted on the basis of the property of the classifier 23. To be specific, the learning data is sorted in advance into "abnormal image" and "normal image" so as to correspond to the "sensitivity" (probability of classifying data including abnormality as abnormal) and "specificity" (probability of classifying normal data as normal) which are the property (detection performance) of the classifier 23, and the sorted learning data is stored.

Though FIG. 4 illustrates a configuration in which the database of a plurality of pieces of learning data (database of learning data group) is formed of the database of "abnormal image" and the database of "normal image", the data configuration of learning data is not limited to this configuration. Each piece of learning data may be tagged regarding whether the data is an "abnormal image" or a "normal image" so that the learning data is stored in a single database. Though not shown in the drawings, the learning data of "abnormal image" is stored according to each detection target (for example, nodule, pneumothorax, or the like). The "abnormal images" may be in databases for respective detection targets, or the "abnormal images" may be stored in a same database in a state of being tagged indicating the detection targets related to the respective images.

Generally, many of medical images are "normal images" and the proportion of "abnormal image" is low. The lesion having fewer cases have fewer "abnormal images".

When learning of the classifier 23 is performed, parts of the plurality of pieces of learning data ("learning data group" in FIG. 4) are extracted to form a batch as the input image data for learning, and input to the classifier 23.

For example, when ten thousand pieces of image data (image data forming a pair with correct answer information) are stored in the "learning data group", 16 images are normally extracted from among the pieces of image data randomly to form a batch, and learning of classifier 23 is performed.

However, when the images are extracted randomly with the original ratio of the "normal image" and "abnormal image" in the "learning data group", there is a high possibility that only the classifier 23 having a low "sensitivity" can be obtained as the learning result since, for example, a single batch is formed of input images that are 12 images of "normal image" and 4 images of "abnormal image".

Thus, in the present embodiment, the learning condition setting section 121 forms a single batch by extracting the learning data from the "learning data group" such that the ratio of "normal image" and "abnormal image" is appropriate according to the property of classifier 23 which was set by the property setting section 11.

For example, in the example shown in FIG. 4, the number of "normal images" is twice or more the number of "abnormal images" in the image data forming the "learning data group". The learning condition setting section 121 extracts 5 images of "normal image" and 11 images of "abnormal image" as the learning input image data forming one batch. The number of images forming one batch and the ratio of "normal image" and "abnormal image" are matters which can be set as needed.

By the above configuration, it is possible to perform learning of classifier 23 with a good balance and obtain the classifier 23 having a high "sensitivity" as the learning result.

When the learning result is evaluated as mentioned later and the property of classifier 23 does not reach a desired level which was set by the property setting section 11, the learning condition setting section 121 adjusts to obtain the classifier 23 having the desired property by performing learning of the classifier 23 again changing the learning condition, such as by changing the ratio of "normal image" and "abnormal image" in the learning input image data forming one batch (for example, in the above example, 1 image of "normal image" and 15 images of "abnormal image" among 16 images).

The setting of learning condition by the learning condition setting section 121 is not limited to this, and various methods can be adopted as needed.

For example, as the way to approach when the learning condition setting section 121 sets the learning condition, the learning condition setting section 121 may set the learning condition to learn the parameter so as to reduce the loss (gap between the actual value and the calculated value).

As for the property which was selected by the user as the detection target requiring a high accuracy and set by the property setting section 11 (lesion, for example, detection target such as the nodule and pneumothorax), for example, the learning condition may be set according to the property set by the property setting section 11 by setting weighting to the loss (gap between the actual value and the calculated value).

Furthermore, when there is a loss (gap between actual value that is correct answer data and calculated value), weighting may be changed between the "normal image" and the "abnormal image". For example, even when there is the same degree of range or number of wrong detections, weighting is made to treating of wrong detection such that the loss is not treated as large when the "normal image" is wrongly determined as an "abnormal image", but the loss is treated as large when the image including an abnormal shadow is wrongly determined as a "normal image". Such a weighting enables learning to make the classifier 23 having a high "sensitivity" that is a probability of classifying the data including abnormality as abnormal.

When learning according to the property which was set for the classifier 23 is performed, the evaluation for the classifier 23 is performed (step S2). To be specific, evaluation is performed by using evaluation data in the evaluating section 13 regarding the sufficiency level of the property which was set by the property setting section 11. The evaluation of the classifier 23 is repeatedly performed in the process of the learning. When the learning is finished, the final evaluation result after learning for each of the classifiers 23 is associated with the classifier 23 and stored in a storage or the like. It is preferable that, when a new classifier 23 to be used in the facility H is set, candidate classifiers having the properties determined as meeting the demand of the present facility H are extracted by the above evaluation results and the candidate classifiers are evaluated. This enables narrowing the candidate of the classifier 23 to be the evaluation target and efficiently evaluating the classifier 23.

As for the classifiers 23 having the evaluation results not satisfying the property condition set by the property setting section 11, it is preferable to change the learning condition and perform learning again. This enables increasing the candidates which satisfy the property condition and can be set as the evaluation target and furthermore as a new classifier 23, and setting an appropriate classifier 23 from among more candidates.

Figure 5:
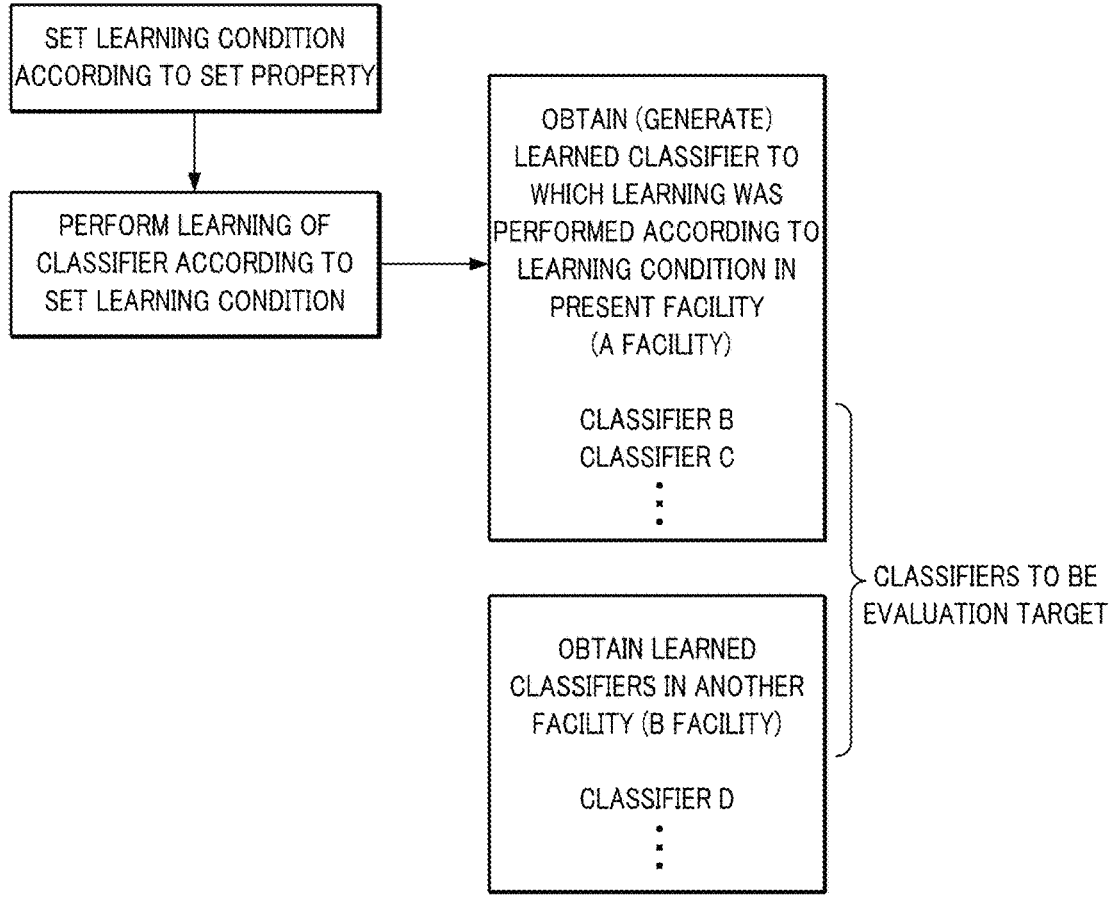
FIG. 5 is an explanation view schematically showing the classifier which is an evaluation target in the present embodiment.

As shown in FIG. 5, the classifier 23 that is the evaluation target of the evaluating section 13 in the present embodiment is a learned classifier 23 to which learning was performed by using the data collected in the present facility H which is a facility to use the classifier 23, or a learned classifier 23 to which learning was performed by using the data collected in another facility H different from the facility to use the classifier 23.

The learned classifier 23 to which learning was performed by using the data collected in the present facility H (for example, A facility) is learned classifiers 23 (in FIG. 5, classifier B, classifier C, etc.) to which the learning condition setting section 121 set the learning condition according to the property set by the property setting section 11 as mentioned above and learning was performed in the present facility H (for example, A facility) according to the set learning condition. The learned classifier 23 to which learning was performed by using the data collected in another facility H is learned classifiers 23 (in FIG. 5, classifier D, etc.) to which learning was performed in the another facility H (for example, B facility).

The classifier 23 to be used in the present facility H is not limited to the classifier learned at the present facility H, and it can be considered to apply the classifier 23 which was already used in another facility and had learning results accumulated, or the classifier 23 and parameters having the experience of being used.

For example, when a manufacturer or the like prepares a database of the association between various classifiers 23 and the property evaluation results of the respective classifiers 23 in advance, the classifiers 23 or the like satisfying the property condition may be extracted as the candidate classifiers to be the evaluation target from outside the present facility H, according to the property of classifier 23 which is set as required by the user in the present facility H.

Figure 6:
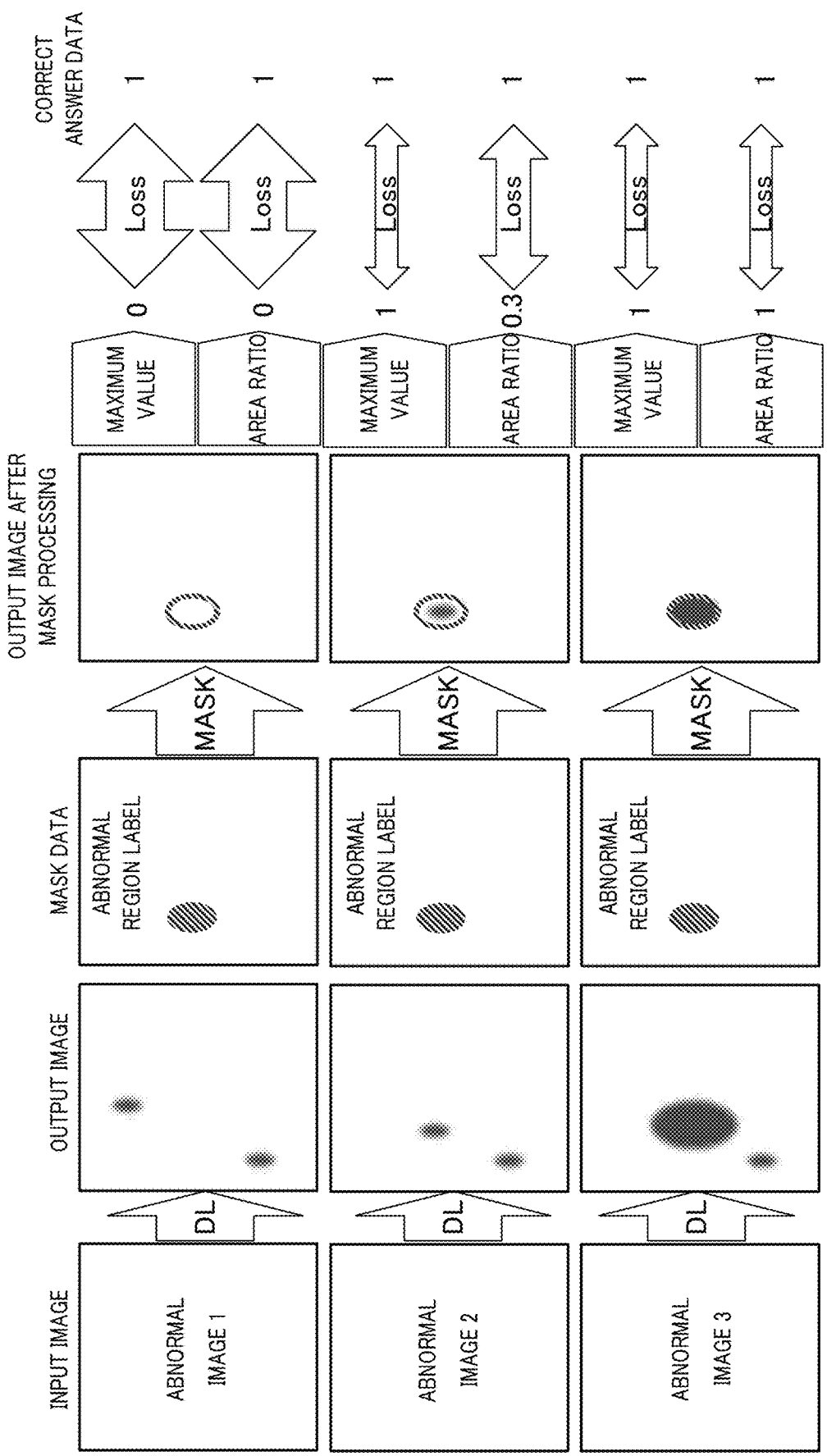
FIG. 6 is an explanation view explaining about loss calculation at the time of learning of classifier when an input image is an "abnormal image"
Figure 7:
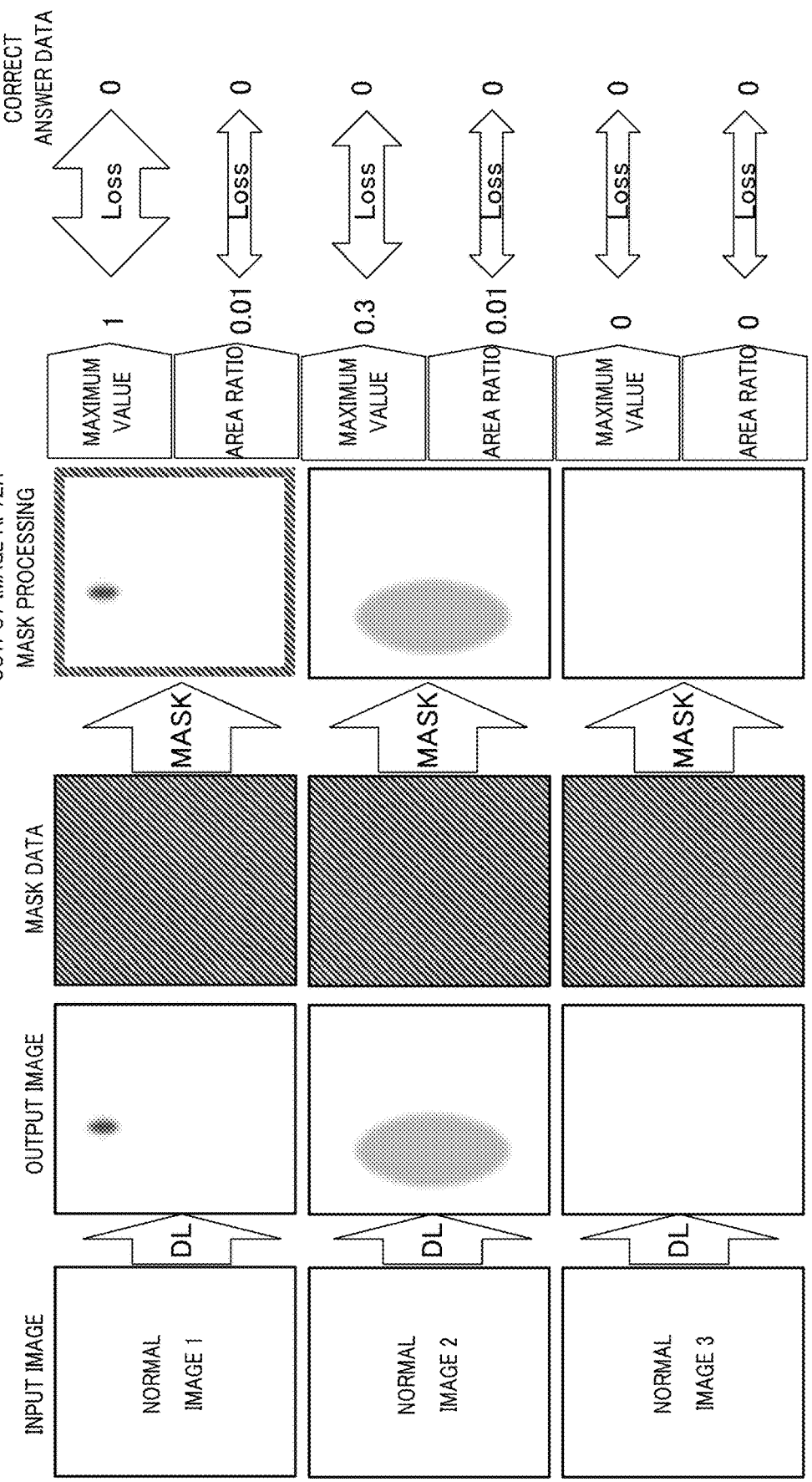
FIG. 7 is an explanation view explaining about loss calculation at the time of learning of classifier when an input image is a "normal image"

FIG. 6 is a view schematically showing loss calculation for determining the property of classifier when the "abnormal image" is input. FIG. 7 is a view schematically showing the loss calculation for determining the property of classifier when the "normal image" is input.

As shown in FIGS. 6 and 7, each input image is input as the evaluation data, and as a result of the deep learning (in FIGS. 6 and 7, "DL"), the output image is output. Then, the loss at the time of learning is calculated by applying the mask data to the output image.

In the present embodiment, as mentioned later, the "maximum value" and "area ratio" of the output image are calculated as the loss.

When the input image is determined by applying the classifier 23, the "maximum value" of the output image (in the present embodiment, "certainty image" as mentioned above) is obtained and the final determination regarding whether or not the input image is the "abnormal image" is performed by whether or not the obtained maximum value exceeds a threshold value. By using the "maximum value", it is possible to improve the determination accuracy. Furthermore, since the determination is made from the output image, it is possible to confirm the region which was the basis of the determination of "abnormal image" in the output image.

However, the evaluation by only the "maximum value" becomes a correct evaluation value even when a large abnormal shadow (lesion part) is detected as a small region, and learning cannot be performed for the size of abnormal shadow (lesion part). Thus, it is not possible to learn regarding the size of the abnormal shadow (lesion part). As for this point, by using the evaluation value of "area ratio" together, detecting a large abnormal shadow (lesion part) as large and a small abnormal shadow (lesion part) as small becomes a correct answer, and it is possible to correctly learn regarding the size of the abnormal shadow (lesion part).

When evaluation is performed also for the border of abnormal shadow (lesion part), by using the evaluation value of the border recognition of the abnormal shadow (lesion part), it is possible to learn regarding not only the presence/absence of the abnormal shadow (lesion part), but also the border of the abnormal shadow (lesion part) (location, size and the like of the abnormal shadow (lesion part)).

First, when the input image is an "abnormal image" including an abnormal shadow, the mask data is set the output image indicating the portion of abnormal shadow. In the mask data, the value of 1 indicating abnormal or the value of 0 indicating normal is set to each pixel. The portion to which 1 is set is the region (mask region) for which the abnormal region label indicating the abnormal shadow is set. When the corresponding mask data is applied to each pixel of the output image of the deep learning (DL), there is obtained the output image (output image after mask processing) corresponding to the region having the mask data of the value of 1. Thus, for an abnormal image, the output result other than the portion of abnormal shadow (region for which the abnormal region label is set) is not used. Thus, it is possible to achieve the reduction of data amount.

The maximum value of the result after multiplication of mask data is then calculated. As for the abnormal image, as shown in FIG. 6, a high abnormal value of any one point of the portion of abnormal shadow (region for which the abnormal region label is set) is determined as the correct answer.

In this point, in the "abnormal image 1" shown in FIG. 6, the loss is large since the output image indicating the abnormal shadow does not include the actual portion of abnormal shadow (region for which the abnormal region label is set). On the other hand, in the "abnormal image 2", since a high abnormal value is shown for a part of the portion of abnormal shadow, the maximum value is 1, and there is no loss. In the "abnormal image 3", the output image indicating the abnormal shadow is in the range wider than the actual portion of abnormal shadow, but determined as the correct answer when the output image is output to contain the actual portion of abnormal shadow. Thus, there is no loss in the abnormal image 3. By setting the correct answer in such a way, the learning is performed to have a higher certainty for the portion of abnormal shadow even when the border of region (mask region) for which the abnormal region label is set is not accurately drawn in the learning which received the above evaluation result.

The portion for which the value of 1 indicating abnormal is not set in the mask data (region for which the abnormal region label is not set) is the region which is not determined to be normal or abnormal (region not used in the learning).

In the calculation of loss, the area ratio of the mask region of the result after mask multiplication (area ratio=sum of output images after mask multiplication (mask processing)/sum of mask regions), that is, the area ratio between the actual value and the calculated value for the portion of abnormal shadow is also calculated.

When the input image is an "abnormal image" including an abnormal shadow, it is configured to be able to detect the entire region (mask region) for which the abnormal region label is set as the portion of abnormal shadow. Thus, when the region detected as the portion of abnormal shadow contains the entire mask region as in the "abnormal image 3", even when the border of mask region cannot be accurately defined (that is, even when the output image after mask multiplication (after mask processing) is in the range wider than the mask region), it is not determined as loss.

On the other hand, when the region detected as the portion of abnormal shadow does not include the mask region as in the "abnormal image 1", and when the region detected as the portion of abnormal shadow is smaller than the mask region as in the "abnormal image 2", the gap amount is the loss.

When the input image is the "normal image" not including the abnormal shadow, the mask data is set to the entire image. In the mask data, the value of 0 indicating normal is set to each pixel. When learning is performed for the "normal image", learning is performed such that the value is 0 at any position of the entire image. Thus, learning is performed to have the value of 0 for the portion of region which is easily wrongly recognized as abnormal shadow (lesion part) in the "normal image", and it is possible to perform learning to correctly recognize the region which is easily wrongly recognized.

In the "normal image", as shown in FIG. 7, when the corresponding mask data is applied to each pixel of the output image of deep learning (DL), there is obtained an output image (output image after mask processing) having the value of 1 for the region which was determined (wrongly determined) as the portion of abnormal shadow.

The maximum value of the result after multiplication of mask data is then calculated. When the image is the "normal image", the height of output certainty as abnormal shadow is the loss.

In this point, in the "normal image 1" shown in FIG. 7, the output image strongly indicating the abnormal shadow is output though the image is actually the "normal image". Thus, the loss is large. On the other hand, in the "normal image 2", though the wide range is determined as an abnormal shadow, the output certainty is weak. Thus, the value is 0.3 which is lower than the "normal image 1" as the maximum value, and the loss is small. When the image is the "normal image 3", since the output image does not show the abnormal shadow, it is the correct answer, and there is no loss.

In the calculation of loss, the area ratio of the mask region of the result after mask multiplication (the area ratio=sum of output images after mask multiplication (mask processing)/sum of mask regions), that is, the area ratio between the actual value and the calculated value for the input image is also calculated.

In the example shown in FIG. 7, the abnormal shadow is wrongly detected in the "normal image 1" and the "normal image 2". The "normal image 2" has a larger size (range) of the detected abnormal shadow than that of the "normal image 1", but as for the "normal image", the size (rang) of the output image output as the portion of abnormal shadow does not influence the loss. Thus, both of the "normal image 1" and the "normal image 2" has the same loss of 0.01.

As a result of evaluating each classifier 23 on the basis of multiple pieces of evaluation data, the evaluating section 13 stores the final evaluation result for each item of the property set by the property setting section 11 in the evaluation result storage region 24 or the like of the storage 32 so as to be associated with the classifier 23.

When the above learning and evaluation are performed to the classifier 23, in the information processing apparatus 3, the display controller 16 controls the display 34 to display the evaluation result (step S3).

FIG. 8 is a view showing an example of the evaluation result list screen displayed on the display.

The evaluation result list screen 34a shown in FIG. 8 treats the classifier 23 which is currently used in the facility ("classifier A" in FIG. 8), and two types of classifiers 23 learned at the present facility H (A facility) ("classifier B" and "classifier C" in FIG. 8) and one type of classifier learned in another facility H ("classifier D" in FIG. 8) as candidates of the new classifier 23. The evaluation results by the evaluating section 13 for the respective classifiers 23 are associated and displayed in a list.

The way of displaying, displayed items, arrangement of the items and the like of the evaluation result list screen 34a are not limited to the illustrated example. The term "list" displaying described in this disclosure is not necessarily limited to displaying all in one screen. For example, "list" displaying includes having items displayed by scrolling in vertical and/or horizontal direction, and includes having a list table as shown in FIG. 8 straddling pages.

FIG. 8 shows an example of displaying a list of evaluation results when the items set as the property of classifier 23 are the "sensitivity" of detecting the "abnormal image" including an abnormal shadow as abnormal for the detection target of "nodule", "pneumothorax", and "tuberculosis", the "specificity" of classifying the normal image as normal, and the processing speed. Among these items, the essential property condition is set that the "sensitivity" for "nodule" is 90% or more and the "specificity" is the current value (that is, 70% which is the property of current classifier A) or more. The desirable property condition is set that the "sensitivity" for "pneumothorax" is 55% or more and the "processing speed" is the current value (that is, 0.5s/image which is the property of current classifier A) or more.

As mentioned above, the display controller 16 uses different displaying methods of the display 34 between when the evaluation result by the evaluating section 13 satisfies the property of classifier 23 set by the property setting section 11 and when the evaluation result does not satisfy the property. In the example shown in FIG. 8, the case of satisfying the set property of classifier 23 is shown by light shading (for example, see the portion of "sensitivity" of 92% of "nodule" in the property of new classifier B), the case of not satisfying the essential property condition is shown by deep shading (for example, see the portion of "sensitivity" of 85% of "nodule" in the property of new classifier C), and the case of not satisfying the desirable property condition is shown by oblique lines (for example, see the portion of "sensitivity" of 50% of "pneumothorax" in the property of new classifier B). Furthermore, the display field regarding the detection target which was determined as not important currently as the detection target by the user (for example, item regarding "tuberculosis" in FIG. 8) may be painted by dark shading so as not to be noticeable.

Each item of the classifier 23 which did not satisfy the essential property condition (for example, see each item of new classifier C) may be painted by dark shading so as not to be noticeable.

The way of displaying is not particularly limited. The type of shading may be changed as in the illustrated example. The color of shading or the color of characters may be changed, or the size and thickness of characters may be changed to display the item to be emphasized so as to be noticeable, for example. The classifiers 23 may be displayed in order from the classifier 23 having a high sufficiency level of the property, or the order (arrangement order) of classifiers 23 displayed in the display screen may be changed.

When the classifier 23 does not satisfy the set condition of property, the color or display manner may be changed according to the level of not satisfying the condition. For example, displaying may be performed with the characters or shading of yellow color when the classifier 23 lacks the property condition by 2% (for example, when the property is 93% for the item requiring the "sensitivity" of 95% or more), and of red color when the classifier 23 lacks the property condition by 10% or more (for example, when the property is 84% for the item requiring the "sensitivity" of 95% or more). Thus, the display is easy to see and understand for the user, and can effectively call attention.

When the classifier 23 does not satisfy the set property condition, warning may be given by characters or sound output, or only the item(s) not satisfying the property may be displayed in a blinking manner on the screen.

Even the classifier 23 which does not satisfy the set property may be set as a new classifier 23 to be used in a facility H when the user compares the classifier with other classifiers 23 for each item and determines that the classifier 23 is appropriate to be used for the present facility H.

For example, there may be a classifier 23 for which the property of item of "essential property condition" is excellent compared to the other classifiers 23 though there is an item having the value insufficient by 5% among the items of "desirable property condition". There may be a classifier 23 that has an item having the value insufficient by 1% among the items of "essential property condition" but shows overall high performance for the other items. When there are classifiers 23 like the above classifiers 23 that the user determines as having no problem when used in the facility H, the classifier 23 can be set as a new classifier 23 to be used in the facility H.

Devising a way to display on the display 34 and displaying a list of evaluation results makes it easy for the user to perform such comparison and consideration and to select an appropriate classifier 23.

When the user selects any of the classifiers 23 as a new classifier 23 in view of the evaluation results, the instruction signal according to the instruction is output to the controller 31, and the classifier setting section 14 sets the selected classifier 23 as the new classifier 23 to be applied in the present facility H (step S4).

To be specific, for example, the display controller 16 causes the display 34 to display the evaluation results, and thereafter causes the display 34 to display the switching/selecting screen of the classifier 23 to urge the user to select the classifier 23.

FIG. 9 is a display screen example of switching and selecting screen of classifier displayed on the display.

For example, as shown in FIG. 9, the switching/selecting screen 34*b* of the classifier 23 is provided with the display field b1 of "essential property condition" to display that "the sensitivity for the nodule is 90%" or the like.

The properties of respective classifiers 23 regarding the "essential property condition" are displayed in the property display field b2. In the example shown in FIG. 9, the item required as the essential condition is "sensitivity for nodule" and the property of each classifier 23 for this item is displayed in the property display field b2. In FIG. 9, the classifier A is currently used, and the candidates of new classifier 23 are classifiers B, C and D. The properties of the classifiers A to D are 80%, 92%, 85% and 90%, respectively.

A check box b3 is provided to each of the classifiers 23, and the classifier A which is being used is checked (painted in FIG. 9) to indicate that the classifier A is currently used. When any of the other classifiers 23 (classifiers B, C and D which are candidates of new classifier 23) is selected (a check mark is input in FIG. 9) and the switching button b4 is operated, the information of the selected classifier 23 is transmitted as the instruction signal to the controller 31.

The switching/selecting screen 34*b* is provided with a comment field b5. For example, as shown in FIG. 9, the classifier 23 which is currently used, the recommended classifier 23, the procedure for switching classifier 23 and the like are displayed in the comment field b5.

The way to display the switching/selecting screen 34*b*, display items, the arrangement of items and the like are not limited to the illustrated example.

For example, when there is a classifier 23 among the displayed classifiers 23 that does not satisfy the "essential property condition", the classifier 23 may be distinguished by displaying in a different color from others, such as red characters.

When the user checks the check box b3 beside the classifier 23 (for example, classifier B) to be switched among the check boxes b3 in the switching/selecting screen 34*b* and operates the switching button b4, the instruction signal of switching the classifier 23 to be used in the facility H from the currently used classifier (for example, classifier A) to the desired classifier 23 selected by the user (for example, classifier B) is input to the controller 31.

When the evaluation result of the selected classifier 23 satisfies the set property condition, the classifier 23 to be used in the facility H is set (updated) to the selected classifier 23 by the classifier setting section 14.

When the evaluation result of the desired classifier 23 (for example, classifier B) selected by the user does not satisfy the set property condition, the user may be warned by displaying a warning message on the display 34, or notifying by sound or the like. As mentioned above, even when the classifier 23 does not satisfy the property condition, when the user wishes to set the classifier 23, the classifier 23 may be set and updated as a new classifier 23 after warning the user.

When the user does not perform any operation of the switching button b4, the classifier 23 which is currently used (for example, classifier A) is applied as the classifier 23 to be used in the facility H.

Though the embodiment illustrates a configuration in which the user manually sets and updates a new classifier 23, the setting and updating of the new classifier 23 may be automatically performed by the controller 31 (classifier setting section 14) of the information processing apparatus 3. In this automatic setting and updating, the classifier 23 having the highest sufficiency level of the set property is automatically set and updated as a new classifier 23. When there are a plurality of classifiers 23 of a same degree of accuracy, the classifier 23 which is highly evaluated for the essential property condition may be selected prior to the other classifier(s) 23.

Various types of rules may be determined in advance. For example, the classifier 23 learned in the present facility is set prior to the other classifier(s) 23 when there are the classifier 23 learned in the present facility and classifier(s) 23 learned in other facility(s). Such a rule may be set as default, or the user may set a rule as needed.

When a new classifier 23 is automatically set by the classifier setting section 14 according to the evaluation result by the evaluating section 13, the displaying of evaluation results shown in step S3 in FIG. 2 may not be performed. Even when the user does not perform any determination or consideration, an appropriate classifier 23 is automatically set.

After a new classifier 23 is set as the classifier 23 to be used in the facility H, the image determining section 15 applies the set classifier 23 to perform image determination.

The classifier 23 to be used in the facility H may be reconsidered and updated to a new classifier 23 as needed.

[Effects]

As descried above, according to the present embodiment, an information processing apparatus 3 including a classifier 23 that is applied for medical treatment data (medical image data in the present embodiment) includes: a property setting section 11 that sets a property of the classifier 23; an evaluating section 13 that evaluates a sufficiency level of the property by using evaluation data for the classifier 23; and a classifier setting section 14 that selects and sets one classifier 23 as the classifier 23 to be used in a facility by referring to an evaluation result by the evaluating section 13.

Thus, by setting the property which is desired in a facility H to use the classifier 23 (for example, detection target to be detected accurately and desired detection performance), it is possible to select and set a classifier 23 that satisfies the property as the classifier 23 to be used in the facility.

Thus, it is possible to set, as the classifier 23 to be used in the facility H, the optimum classifier 23 that is excellent in desired discrimination accuracy and most helpful in supporting a doctor or the like in consideration of the manner of using the classifier 23 and the usage in each facility H.

In the present embodiment, the "property" of the classifier 23 includes a detection target to be detected and a detection performance for the detection target.

Thus, it is possible to set, as the classifier 23 to be used in the facility H, the classifier 23 that has a desired detection accuracy of an abnormal shadow (lesion) to be especially discriminated accurately in the facility H using the classifier 23.

In the present embodiment, the "detection performance" of the classifier 23 includes a sensitivity that is a probability of classifying data including abnormality as abnormal and a specificity that is a probability of classifying normal data as normal.

Thus, it is possible to set, as the classifier 23 to be used in the facility H, the classifier 23 that has the optimum property according to whether the important detection performance is "sensitivity" or "specificity", whether both of the "sensitivity" and the "specificity" need a high accuracy, and the manner of using the classifier 23 and the usage in each facility H.

In the present embodiment, the classifier 23 that is an evaluation target of the evaluating section 13 is a learned classifier 23 to which learning was performed by using data collected in a present facility that is the facility H to use the classifier 23.

Thus, it is possible to perform learning (machine learning) according to the manner of using the classifier 23 and the usage in the present facility H, and set the classifier 23 having the optimum property for the facility H as the classifier 23 to be used in the facility H.

In the present embodiment, the classifier 23 that is an evaluation target of the evaluating section 13 is a learned classifier 23 to which learning was performed by using data collected in a facility different from the facility to use the classifier 23.

Thus, even when a sufficient amount of learning data cannot be secured in the present facility only, it is possible to obtain a large amount of data necessary to perform learning (machine learning) with a high accuracy. By performing sufficient learning with the large amount of learning data, it is possible to set the classifier 23 having an excellent property as the classifier to be used in the facility H.

In the present embodiment, there is provided a learning condition setting section 121 that sets a learning condition of the classifier 23.

Thus, it is possible to obtain the classifier 23 which was learned at the appropriate learning condition.

In the present embodiment, setting of the learning condition by the learning condition setting section 121 is performed based on the property of the classifier 23 which was set by the property setting section 11.

The property of classifier 23 changes according to the learning condition at the time of learning, and it is necessary to learn at an appropriate condition in order to obtain the classifier 23 of a high accuracy. However, it is difficult for the user to determine and set the learning condition to obtain the desired property, and trial and error for determining and setting the learning condition is troublesome and burden on the user. As for this point, by setting the learning condition on the basis of the property of classifier 23 which was set by the property setting section 11 as in the present embodiment, it is possible to automatically set the learning condition for obtaining the classifier 23 having a desired property without bothering the user.

In the present embodiment, learning data that is used in learning of the classifier 23 is sorted based on the property of the classifier 23, and the learning condition setting section 121 extracts the learning data according to the property of the classifier 23 that was set by the property setting section 11.

One of important learning conditions for obtaining the classifier 23 having a desired property is the configuration of learning data used in learning of the classifier 23, but it is difficult for the user to determine and set the learning data configuration, and the try and error for determining and setting the learning data configuration is troublesome and burden on the user. As for this point, by the learning condition setting section 121 automatically extracting learning data on the basis of the property of classifier 23 which was set by the property setting section 11 as in the present embodiment to perform learning of the classifier 23 by the learning data, it is possible to automatically obtain the classifier 23 having the desired property without bothering the user.

In the present embodiment, there is further provided a display 34 that displays the properties of the classifiers 23 and the evaluation results by the evaluating section 13 regarding the classifier 23.

Thus, the user can easily compare and consider the properties of respective classifiers 23, and easily select the appropriate classifier 23.

In the present embodiment, the display 34 uses different displaying methods for the evaluation result that satisfies the property of the classifier 23 set by the property setting section 11 and for the evaluation result that does not satisfy the set property of the classifier 23. That is, for example, the displaying method is devised to display with a green color when the evaluation result satisfies the property of classifier 23 set by the property setting section 11 and to display with yellow or red color when the evaluation result does not satisfy the set property. Thus, the user can intuitively grasp the evaluation result of properties of respective classifiers 23 by merely seeing the displaying of display 34, and the user can easily compare and consider the properties of classifiers 23 and easily select the appropriate classifier 23.

According to the embodiment, it is possible to set the classifier appropriate for the facility to use the classifier, according to the property required in the facility.

Though the embodiment of the present invention has been described above, the present invention is not limited to the embodiment, and various modifications can be made within the scope of the present invention.

For example, in each of the above embodiment, the medical treatment data is data of a medical image, and the abnormal data to be discriminated by the classifier 23 is an abnormal shadow appearing in the image. However, the medical treatment data is not limited to image data.

For example, the medical treatment data may be various types of sound data obtained by auscultation or the like (for example, heart tone, heart murmur, carotid artery murmur and breathing sound obtained by chest auscultation, abdominal vascular murmur and bowel sound obtained by abdominal auscultation), or may be various types of waveform data (for example, time series information of waveform of electrocardiogram). The medical treatment data may be character data such as electronic medical record information and examination information which was input by a doctor or the like.

When the medical treatment data is sound data, the abnormal data is an abnormal sound included in the sound data, for example. When the medical treatment data is waveform data, the abnormal data is, for example, an abnormal waveform included in the waveform data. When the medical treatment data is character data, the abnormal data is a specific character string representing an abnormal state (for example, name of a disease), for example.

When the medical treatment data is data other than data of a medical image in such a way and it is necessary to generate pseudo data due to the lack of learning data or the like, there is applied a section that automatically generates data corresponding to medical treatment data such as the sound data, waveform data and character data, not a section that generates image data of GAN or the like.

The medical treatment data is not limited to the medical image captured by the medical image capturing apparatus. The present invention can also be applied to discrimination by the classifier for general image.

In the embodiment, the image management server 7 including a medical image database 71 storing medical image data or the like is provided in the medical image system 100 in the facility H. However, the medical image database 71, the image management server 7 including the medical image database 71, and the like can be provided in a server device outside the facility H which is connected to transmit and receive information via the network NT (see FIG. 1).

By providing the medical image database 71 storing a large amount of data and the image management server 7 including the medical image database 71 or the like separately from the medical image system 100 in the facility H, it is possible to reduce the load on the medical image system 100.

Although embodiments of the present invention have been described and illustrated in detail, the disclosed embodiments are made for purposes of illustration and example only and not limitation. The scope of the present invention should be interpreted by terms of the appended claims.

What is claimed is:

1. An information processing apparatus comprising:
a classifier that is applied for medical treatment data; and
a hardware processor that:
sets a property of the classifier;
evaluates a sufficiency level of the property by using evaluation data for the classifier;
selects and sets one classifier as the classifier to be used in a facility by referring to an evaluation result; and
sets a learning condition of the classifier based on the set property of the classifier,
wherein the property includes a detection performance for a detection target,
the detection performance includes both or one of a sensitivity that is a probability of classifying data including an abnormality as abnormal and a specificity that is a probability of classifying normal data as normal, and
the hardware processor extracts learning data used in learning according to the property of the classifier such that a ratio of the data including the abnormality and the normal data is appropriate.

2. The information processing apparatus according to claim 1, wherein the classifier that is an evaluation target is a learned classifier to which learning is performed by using data collected in a present facility that is the facility to use the classifier.

3. The information processing apparatus according to claim 1, wherein the classifier that is an evaluation target is a learned classifier to which learning is performed by using data collected in a facility different from the facility to use the classifier.

4. The information processing apparatus according to claim 1, wherein
the property further includes the detection target to be detected,
learning data that is used in learning of the classifier is sorted based on the property of the classifier, and
the hardware processor extracts the learning data according to the set property of the classifier.

5. The information processing apparatus according to claim 4, further comprising a display that displays the property of the classifier and the evaluation result regarding the classifier.

6. The information processing apparatus according to claim 5, wherein the display uses different displaying methods for the evaluation result that satisfies the property of the classifier set by the hardware processor and for the evaluation result that does not satisfy the set property of the classifier.

7. An information processing method comprising:
property setting that is setting a property of a classifier applied for medical treatment data;
evaluating that is evaluating a sufficiency level of the property by using evaluation data for the classifier;
classifier setting that is selecting and setting one classifier as the classifier to be used in a facility by referring to an evaluation result of the evaluating;
setting a learning condition of the classifier based on the set property of the classifier, wherein the property includes a detection performance for a detection target, and the detection performance includes both or one of a sensitivity that is a probability of classifying data including an abnormality as abnormal and a specificity that is a probability of classifying normal data as normal; and
extracting learning data used in learning according to the property of the classifier such that a ratio of the data including the abnormality and the normal data is appropriate.

8. A non-transitory recording medium storing a computer readable program causing a computer of an information processing apparatus to perform:
property setting that is setting a property of a classifier applied for medical treatment data;
evaluating that is evaluating a sufficiency level of the property by using evaluation data for the classifier;
classifier setting that is selecting and setting one classifier as the classifier to be used in a facility by referring to an evaluation result of the evaluating;
setting a learning condition of the classifier based on the set property of the classifier, wherein the property includes a detection performance for a detection target, and the detection performance includes both or one of a sensitivity that is a probability of classifying data including an abnormality as abnormal and a specificity that is a probability of classifying normal data as normal; and
extracting learning data used in learning according to the property of the classifier such that a ratio of the data including the abnormality and the normal data is appropriate.

9. The information processing apparatus according to claim 1, wherein
the property defines a specific abnormality to be detected by playing and the sensitivity for the specific abnormality,
the evaluation data including sensitivities of each of various abnormalities including the specific abnormality, wherein each of the sensitivities is a probability of classifying data including a respective one of the various abnormalities as abnormal; and
the hardware processor selects and sets one classifier as the classifier to be used in the facility that meets the sensitivity of the specific abnormality by referring to the evaluation result.

* * * * *